United States Patent [19]

Tong

[11] 4,108,859

[45] Aug. 22, 1978

[54] MICROBICIDAL (PYRIDINYLAMINO) ALKYL GUANIDINES

[75] Inventor: Yulan C. Tong, Walnut Creek, Calif.

[73] Assignee: The Dow Chemical Company, Midland, Mich.

[21] Appl. No.: 804,038

[22] Filed: Jun. 6, 1977

[51] Int. Cl.$^2$ ............................................. C07D 213/53
[52] U.S. Cl. ................................. 260/296 R; 424/263; 260/564 E
[58] Field of Search ......................... 260/564 F, 296 R

[56] References Cited

U.S. PATENT DOCUMENTS

| | | | |
|---|---|---|---|
| 1,672,029 | 6/1928 | Heyn | 260/564 F |
| 3,200,151 | 8/1965 | Spickett et al. | 260/564 F |
| 3,313,813 | 10/1963 | Cragoe | 260/250 R |
| 3,920,822 | 11/1975 | Durant et al. | 424/263 |
| 4,034,101 | 7/1977 | Durant et al. | 260/296 R X |

*Primary Examiner*—John D. Randolph
*Attorney, Agent, or Firm*—Robert R. Stringham

[57] ABSTRACT

Acid salts of N,N'-dialkyl-N''-(substituted pyridyl)aminoalkylguanidines constitute a novel class of compounds having good microbicidal activity, particularly against microorganisms which attack paints. These guanidines are prepared by reacting corresponding N-(chloropyridyl)alkanediamines with N,N'-dialkyl-S-ethylthiouronium iodide in an inert, polar solvent.

11 Claims, No Drawings

MICROBICIDAL (PYRIDINYLAMINO) ALKYL GUANIDINES

BACKGROUND OF THE INVENTION

U.S. Pat. No. 3,920,822 discloses pharmacologically active cyanoguanidines of the formula

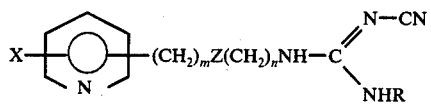

wherein R is H or lower alkyl, X is H, lower alkyl, —CF$_3$, —OH, halogen or amino, Z is —S— or —O—, m is 0, 1 or 2 and n is 2 or 3, the sum of m and n being 3 or 4.

Diuretic halopyrazinoyl guanidines of the formula

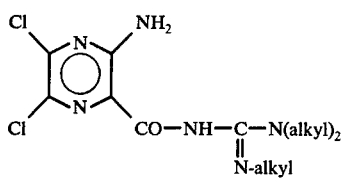

are disclosed in U.S. Pat. No. 3,313,813.

No examples of N-heterocyclic guanidines more closely resembling the compounds of the present invention have been found in the literature.

OBJECTS OF THE INVENTION

The primary object of the present invention is to provide a novel class of (pyridinylamino)alkyl guanidine salts having utility as microbicides.

An additional object is to provide a novel process for making such compounds.

A further object is to provide microbicidal guanidines which can readily be prepared (as acid addition salts) from readily available chlorinated pyridine compounds.

Another object is to provide microbicidal compounds which are particularly active against fungi which attack paints.

Still other objects will be made apparent, to those skilled in the art, by the following specifications and claims.

SUMMARY OF THE INVENTION

The present invention is a group of compounds and a method for their preparation. More specifically, the compounds may be defined as (pyridinylamino) alkyl guanidine salts of the formula

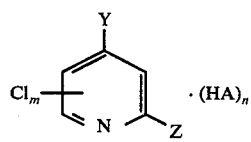

wherein:
one of Y and Z is —H, —Cl, —CCl$_3$ or —CN and the other is —NH—R$^1$—N=C(NHR$^2$)$_2$,
m is 1 to 3,
n is 1 or 2
R$^1$ is an alkylene group of 3 to 8 carbons,
R$^2$ is —CH$_3$ or —C$_2$H$_5$, independently in each occurrence, and
HA is pharmaceutically acceptable acid.

The guanidine salts of the present invention are white or light colored solids, or are occasionally obtained as difficultly crystallizeable oils. They are generally soluble in polar organic solvents.

The invention also embraces the method of preparing a compound of the preceding formula which comprises reacting a corresponding N-(chloropyridinyl)alkanediamine of the formula

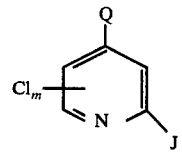

wherein one of Q and J is —H, —Cl, —CCl$_3$ or —CN and the other is —NH—R$^1$—NH$_2$, R$^1$ being as above defined, with an N,N'-dialkyl-S-ethyl thiouronium iodide of the formula

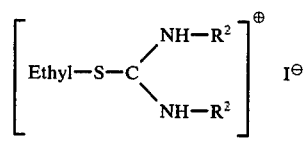

wherein R$^2$ is as above defined, by maintaining a solution in acetonitrile of said alkanediamine and thiouronium iodide at a temperature of at least 75° C. for at least ten hours.

DETAILED DESCRIPTION

Preparation of Starting Materials

The N-(chloropyridinyl)alkanediamine reactants (as above defined) in which Q is —NH—R$^1$—NH$_2$ may be prepared by reacting the corresponding diamine, H$_2$N—R$^1$—NH$_2$, with a chloropyridine of the formula

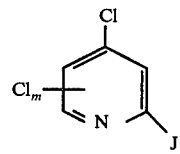

J being as above defined.

The N-(chloropyridinyl)alkanediamine reactants in which J is —NH—R$^1$—NH$_2$ may be prepared by reacting the corresponding diamine with a chloropyridine of the formula

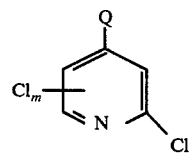

provided that Q is not —Cl. If Q is Cl, the chloropyridine should be converted to the corresponding N-oxide, before the reaction with the diamine is carried out, and the -oxide oxygen subsequently removed (as by treatment with TiCl₃ in CH₃OH/H₂O, for example). In this manner, a chlorine in the 2 (or 6) position may preferentially be replaced by the —NH—R¹—NH₂ group, even though chlorine in the 4 position is ordinarily more reactive.

In those instances in which chlorines are present in both the 2 and 6 positions and the ring is not identically substituted (or unsubstituted) in the 3 and 5 positions, the reaction with the diamine will generally produce mixtures of isomeric products. However, these mixtures can be resolved by known methods, such as fractional crystallization, preparative chromatography, etc. When the N-oxide route is taken under this circumstance, the isomer separation may be found in some instances to be more easily affected prior to removal of the oxide oxygens.

The reaction between the chloropyridine reactant and the diamine is conveniently carried out by gradually adding a solution of the chloropyridine in THF (tetrahydrofuran) to a solution of the diamine in the same solvent, and allowing the resulting mixture to stir at room temperature for from 24 to 90 hours. The resulting hydrochloride salt is recovered by evaporating off the THF and is then dissolved in water. The solution is made alkaline and the N-(chloropyridyl)alkane diamine is extracted (as the free base) with a water immiscible solvent such as methylene chloride. The solution is dried and the free base recovered therefrom as such (by evaporation) or by precipitating it as a salt, as by introduction of anhydrous HCl in diethyl ether.

In an alternative method of preparing the N-(chloropyridinyl)alkane diamine intermediates, advantage is taken of the ease of nucleophilic displacement of methylsulfonyl substituents in the 2, 6 or 4 positions of pyridine rings substituted with electronegative groups such as —Cl, —CN and —CCl₃. (Methods of making the methylsulfonyl compounds are well known.) THF is also conveniently used as a medium for the latter reaction.

The N,N″-dialkyl-S-ethyl thiouronium iodide reactant is readily prepared in adequate purity by refluxing a methanol solution of the corresponding N,N′-dialkyl-thiourea and about a 20% percent excess of ethyl iodide for several hours and then stripping off the solvent.

Preparation of the Guanidine Compounds of the Invention

The reaction may be exemplified as follows:

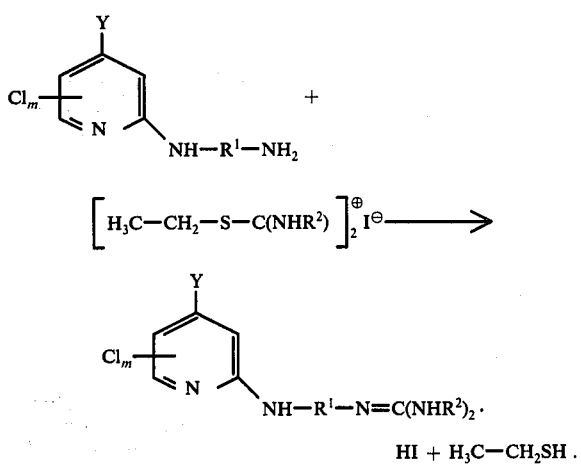

The N-(chloropyridyl)alkanediamine and the thiouronium salt are dissolved in an inert, suitably polar solvent. The solution is heated as necessary to establish a temperature at which a satisfactory reaction rate is attained and is then maintained at that temperature until a satisfactory amount of the guanidine compound has formed. The latter product may be recovered by conventional work-up procedures. In some instances, the product precipitates as formed or upon cooling the reaction mixture, and is simply filtered out and dried.

The N-(chloropyridyl)alkanediamine may be employed in the reaction as an acid salt. However, in an instance in which this was done, the resulting product was a mixed HCl, HI salt of the guanidine. It is generally preferable to introduce the amine reactant as the free base, or at least to liberate it as such in situ from an acid salt.

Acetonitrile is the preferred medium for the reaction. However, any sufficiently polar compound or mixture of compounds which gives a liquid solution at the desired reaction temperature and does not detrimentally effect the production or recovery of the desired compound to an intolerable degree may be employed.

The reaction is relatively slow, even at the reflux temperature (~82° C. at 760 mm Hg) of acetonitrile. Contact times of from 15 to 24 hours at the latter temperature have been found to result in product yields ranging from about 45 to about 75% of theoretical (based on charge). Addition of triethyl amine, in an attempt to speed up the reaction by reducing the activity of the evolved C₂H₅SH, proved ineffective.

Higher boiling solvents, i.e., nitriles or comparably polar solvents of other types, such as benzonitrile, n-butanol, dimethylsulfoxide and dimethyl formamide, for example, can be used but work-up of the reaction mixture will be correspondingly less facile.

It is convenient but not essential to carry out the reaction at reflux and higher boiling solvents may be employed at temperatures below their boiling points. Similarly, although ambient pressures are convenient, the reaction may be carried out at sub- or supra-atmospheric pressures.

Those compounds of the invention, as defined earlier herein, in which R¹ is —(CH₂)₆— are preferred as exhibiting a higher degree of microbicidal activity against more organisms. Similarly, those compounds in which the aminoalkylguanidine substituent is located in the alpha position relative to the ring nitrogen. Among the latter, salts of the specific compound, N,N′-dimethyl-N″-(6-((3,5,6-trichloro-2-pyridyl)amino)-hexyl)guanidine, (with pharmaceutically acceptable acids) are most preferred.

Another preferred class of compounds are those of the invention, as defined earlier herein, in which the one of Y and Z which is not —NH—R¹—N=C(NHR²)₂ is —CN or —CCl₃. Also, those compounds in which R² is methyl, the same in both occurrences, are preferred over those in which R² is ethyl in either or both occurrences.

Preferred among the pharmaceutically acceptable acid components of the salts are hydrogen chloride, hydrogen bromide, hydrogen iodide, sulfuric acid and phosphoric acid.

EXAMPLES

Preparations of Intermediates

EXAMPLE 1 -
N-(3,5,6-Trichloro-2-pyridinyl)-1,6-hexanediamine, monohydrochloride 24.2 grams (0.112 mole) of 2,3,5,6-tetrachloropyridine was added portionwise to a stirring solution of 1,6-hexanediamine (23.2 grams; 0.2 mole) in 300 ml. of THF. The mixture was stirred overnight at room temperature, then evaporated to dryness under reduced pressure. A solution of the residual material in water was made alkaline with $K_2CO_3$ and extracted with $CH_2Cl_2$. The organic layer was dried and evaporated to dryness and the residue dissolved in diethyl ether. Acidification with hydrogen chloride (in ether) precipitated 24.6 grams (66% of theory) of the title compound, a white solid melting at 124°–5° C.:

Anal. Calcd. for $C_{11}H_{16}Cl_3N_3.HCl$: C, 39.66; H, 5.15; N, 12.61. Found: C, 39.90; H, 5.06; N, 12.64.

EXAMPLE 2 -
N-(2,3,5,6-Tetrachloro-4-pyridinyl)-1,4-butanediamine monohydrochloride A solution of 25.1 g (0.1 mole) of pentachloropyridine in 100 ml. of THF was added slowly to a solution of 26.5 g. (0.3 mole) of 1,4-butanediamine in THF at room temperature and stirred for 90 hrs. Worked up as in the preceding example, the reaction mixture gave 21 g. (62%) of the title compound, melting at 218°–9°.

Anal. Calcd. for $C_9H_{11}Cl_4N_3.HCl$: C, 31.83; H, 3.56; N, 12.39. Found: C, 32.15; H, 3.78; N, 12.47.

EXAMPLE 3 -
N-(2,3,5,6-Tetrachloro-4-pyridinyl)-1,3-propanediamine, monohydrochloride Using the same procedure as in Example 2, 25.1 g. (0.1 mole) of pentachloropyridine in 200 ml. of THF was caused to react with 22.3 g. (0.3 mole) of 1,3-propanediamine in 200 ml. of THF to give 18.6 g. (57%) of the title compound, melting at 248°–9°.

Anal. Calcd. for $C_8H_9Cl_4N_3.HCl$: C, 29.52; H, 3.10; N, 12.91. Found: C, 29.74; H, 3.36; N, 12.82.

EXAMPLE 4 -
N-(2,3,5,6-Tetrachloro-4-pyridinyl)-1,6-hexanediamine

Using the method of Example 2, 100.5 g. (0.4 mole) of pentachloropyridine in 800 ml. of THF was caused to react with 140 g. (1.2 mole) of 1,6-hexanediamine in 800 ml. of THF. The hydrochloride salt failed to crystallize. It was dissolved in water and the solution made alkaline with NaOH and extracted with diethyl ether. The ether solution was dried and concentrated to give the title compound as an oil which was analyzed, with the following results.

Anal. Calcd. for $C_{11}H_{15}Cl_4N_3$: C, 39.90; H, 4.57; N, 12.69. Found: C, 39.61; H, 4.55; N, 12.66.

EXAMPLE 5 -
N-(2,3,5-Trichloro-4-pyridinyl)-1,6-hexanediamine

Using the same procedure as in Example 2, 21.7 g. (0.1 mole) of 2,3,4,5-tetrachloropyridine in 100 ml. of THF was caused to react with 34.9 g. (0.3 mole) of 1,6-hexanediamine in 200 ml. of THF. The free base so obtained analyzed poorly. It was converted to the picric acid salt of the title compound, liberated with base, and reanalyzed.

Anal. Calcd. for $C_{11}H_{16}Cl_3N_3$: C, 44.54; H, 5.44; N, 14.29. Found: C, 43.94; H, 4.94; N, 14.29.

EXAMPLE 6 -
4-((6-Aminohexyl)amino)-3,5,6-trichloro-2-pyridinecarbonitrile, monohydrochloride Using the procedure of Example 2, 24.2 g. (0.1 mole) of tetrachloro-2-pyridine-carbonitrile in 200 ml. of THF was caused to react with 34.9 g. (0.3 mole) of 1,6-hexanediamine in 200 ml. of THF to give 27 g. (75%) of the title compound, which melted over the range 120°–4° C.

Anal. Calcd. for $C_{12}H_{15}Cl_3N_4.HCl$: C, 40.24; H, 4.50; N, 15.65. Found: C, 40.89; H, 4.63; N, 15.83.

EXAMPLE 7 -
N-(2,3,5,6-Tetrachloro-4-pyridinyl)-1,5-pentanediamine monohydrochloride Using the procedure of Example 2, 25.1 g. (0.1 mole) of pentachloropyridine was caused to react with 30.6 g. (0.3 mole) of 1,5-pentanediamine in 300 ml. of THF to give 13.5 g. (38%) of the title compound, a solid melting over the range 155°–8°.

Anal. Calcd. for $C_{10}H_{13}Cl_4N_3.NCl$: C, 33.98; H, 3.99; N, 11.89. Found: C, 34.42; H, 4.11; N, 11.89.

EXAMPLE 8 -
N-(2,3,5,6-Tetrachloro-4-pyridinyl)-1,5-pentanediamine 1,5-Pentanediamine, 30.6 g. (0.3 mole) was dissolved in 300 ml. of THF. To this was added in small portions 28.5 g. (0.097 mole) of 4-methylsulfonyl-2,3,5,6-tetrachloropyridine and the resulting solution was stirred at room temperature for 2 days. The reaction mixture was evaporated to dryness and the residue mixed with 100 ml. of 1N NaOH and a comparable volume of diethyl ether. 25.7 g. of ether-insoluble and base-insoluble material (melting range 103°–4° C.) was collected by filtration and designated as the desired product on the basis of its IR and NMR spectra.

Anal. Calcd. for $C_{10}H_{13}Cl_4N_3$: C, 37.88; H, 4.13; N, 13.25. Found: C, 38.12; H, 4.19; N, 13.14.

EXAMPLE 9 -
N-(2,3,5,6-Tetrachloro-4-pyridinyl)-1,7-heptanediamine picrate 1,7-Heptanediamine, 25 g. (0.192 mole), was dissolved in 200 ml. of THF and stirred at room temperature. 4-Methylsulfonyltetrachloropyridine, 21.9 g. (0.074 mole) was added in small portions and stirring was continued for 3 days. The reaction mixture was evaporated to dryness, diluted with 80 ml. of 1N NaOH and extracted with diethyl ether. The ether extracts were combined and washed with water until the washing was nearly neutral. The ether solution was diluted with dichloromethane, dried and acidified with picric acid to give 14 g. of the title product, melting at 174°–6° C.

Anal. Calcd. for $C_{12}H_{17}Cl_4N_3.C_6H_3N_3O_7$: C, 37.65; H, 3.51; N, 14.64. Found: C, 37.86; H, 3.62; N, 14.51.

EXAMPLE 10 -
N-(6-Chloro-4-trichloromethyl-2-pyridinyl)-1,6-hexanediamine picrate 2,6-Dichloro-4-trichloromethylpyridine, 26.5 g. (0.1 mole), was added in small portions to a solution of 34.9 g. (0.3 mole) of 1,6-hexanediamine in 300 ml. of THF. The reaction mixture was heated to boiling and refluxed for 19 hrs. When worked up as in the preceding example, the mixture gave 8.3 g. (14%) of the title product, melting range 130°–5° C.

Anal. Calcd. for $C_{12}H_{17}Cl_4N_3.C_6H_3N_3O_7$: C, 37.65; H, 3.51; N, 14.64. Found: C, 36.98; H, 3.21; N, 15.06.

EXAMPLE 11 -
N-(3,5-Dichloro-2-trichloromethyl-4-pyridinyl)-1,6-hexanediamine monohydrochloride Using the procedure of Example 2, 30.4 g. (0.1 mole) of 3,4,5-trichloro-2-trichloromethylpyridine was caused to react with 34.9 g. (0.3 mole) of 1,6-hexanediamine in 300 ml. of THF to give 8 g. (19%) of the title compound, melting at 137°–8° C.

Anal. Calcd. for $C_{12}H_{16}Cl_5N_3.HCl$: C, 34.64; H, 4.12; N, 10.10. Found: C, 34.97; H, 4.23; N, 10.08.

EXAMPLE 12 - N,N'-Dimethyl-S-ethyl-thiouronium iodide. Reagent "A"

In 100 ml of methanol were mixed 52 g (0.5 mole) of N,N'-dimethylthiourea and 95 g (0.61 mole) of iodoethane. The reaction mixture was heated to boiling under reflux for 4 hours. The solvent was removed under reduced pressure and the crystalline residual material used without further purification.

Preparation of the Guanidines

EXAMPLE 13 -
N,N'-Dimethyl-N''-(3-((tetrachloro-4-pyridyl)amino)propyl)guanidine, hydrochloride, hydroiodide (I)

A mixture of 9.8 g (0.03 mole) of 3-(tetrachloro-4-pyridyl)aminopropylamine hydrochloride, 7.8 g (0.03 mole) of A, and 10 g (0.1 mole) of triethylamine in 100 ml of acetonitrile was heated to boiling under reflux for 15 hours. After cooling, the solid was collected and dried to give 9.5 g of the title product (74.5%) as indicated by IR and NMR spectra.

Anal. Calcd. for $C_{11}H_{14}Cl_4N_5 \cdot \frac{2}{3} HCl \cdot \frac{1}{3} HI$: C, 31.08; H, 3.56; Cl, 38.93; I, 9.95; N, 16.48. Found: C, 31.26; H, 3.79; Cl, 39.52; I, 9.58; N, 16.48.

EXAMPLE 14 -
N,N'-Dimethyl-N''-(6-((2,3,5-trichloro-4-pyridyl)amino)hexyl)-guanidine, hydrochloride, hydrate (II)

6,(2,3,5-Trichloro-4-pyridyl)aminohexylamine, 7.1 g (0.024 mole) and 6.2 g (0.024 mole) of A were mixed in 100 ml of acetonitrile and heated to boiling under reflux for 5 hours. At this point 5 ml of triethylamine was added and heating was continued for another 24 hours. The reaction mixture was evaporated to dryness to leave as a residue a yellow gum which was partitioned with water and dichloromethane. The title compound precipitated at the interface as a white solid and was collected by filtration and dried; 7.8 g (63%); melting range 109°–110° C.

Anal. Calcd. for $C_{14}H_{22}Cl_3N_5.HI.H_2O$: C, 32.80; H, 4.92; N, 13.66. Found: C, 32.79; H, 4.69; N, 13.49.

EXAMPLE 15 -
N,N'-Dimethyl-N''-(6-((3,5,6-trichloro-2-pyridyl)amino)hexyl)-guanidine, hydroiodide (III)

6-(3,5,6-Trichloro-2-pyridyl)aminohexylamine, 4.0 g (0.014 mole), and 3.5 g (0.013 mole) of A were dissolved in 50 ml. of acetonitrile, heated to boiling and refluxed 24 hours. Worked up as in Example 13, the reaction mixture gave 3.5 g (50%) of the title compound, melting at 144°–5° C.

Anal. Calcd. for $C_{14}H_{22}Cl_3N_5.HI$: C, 33.99; H, 4.69; N, 14.16. Found: C, 33.77; H, 4.55; N, 13.85.

EXAMPLE 16 -
N,N'-Dimethyl-N''-(6-((2,3,5-trichloro-6-cyano-4-pyridyl)-amino)hexyl)-guanidine, hydroiodide, hydrate (IV)

6-(2,3,5-Trichloro-6-cyano-4-pyridyl)aminohexylamine hydrochloride, 17.5 g (0.049 mole) was dissolved in water, mixed with $CH_2Cl_2$ and made alkaline with 13.8 g (0.1 mole) of $K_2CO_3$. The organic layer was separated, dried and evaporated to dryness to give a yellow oil. The residual oil was dissolved in 100 ml of acetonitrile and caused to react with 11.5 g (0.44 mole) of A at reflux for 24 hours. Worked up as in Example 13, the mixture gave 17.5 g (74%) of the title product; melting range 93°–7° C. (with decomposition).

Anal. Calcd. for $C_{15}H_{21}Cl_3N_6.HI.H_2O$: C, 33.51; H, 4.50; N, 15.63. Found: C, 33.68; H, 4.10; N, 14.91.

EXAMPLE 17 -
N,N'-Dimethyl-N''-(6((tetrachloro-4-pyridyl)amino)hexyl)guanidine, hydroiodide (V)

6-(Tetrachloro-4-pyridyl)aminohexylamine, 8.8 g (0.026 mole) was caused to react with 6.7 g (0.026 mole) of A according to the procedure of Example 13 and gave 1.4 g (10%) of the title product, melting at 141°–2° C.

Anal. Calcd. for $C_{14}H_{21}Cl_4N_5.HI$: C, 31.78; H, 4.19; N, 13.24. Found: C, 31.97; H, 4.17; N, 13.13.

EXAMPLE 18 -
N''-(6-((3,5-dichloro-2-trichloromethyl-4-pyridyl)amino)hexyl)-N,N'-dimethyl-guanidine, hydroiodide (VI)

6-(3,5-Dichloro-2-trichloromethyl-4-pyridyl)-aminohexylamine, 17 g (0.045 mole), was caused to react with 10.7 g (0.041 mole) of A in 50 ml. of acetonitrile according to the procedure of Example 14 and gave 13.4 g (57%) of the title product, melting at 85°–7° C.

Anal. Calcd. for $C_{15}H_{22}Cl_5N_5.HI$: C, 31.19; H, 4.01; N, 12.13. Found: C, 31.20; H, 4.23; N, 11.57.

EXAMPLE 19 -
N''-(6-((6-Chloro-4-trichloromethyl-2-pyridyl)amino)hexyl)N,N'-dimethyl-guanidine, hydroiodide (VII)

6-(6-Chloro-4-trichloromethyl-2-pyridyl)-aminohexylamine, 15.5 g (0.045 mole), was caused to react with 10.7 g (0.041 mole) of A in 50 ml of acetonitrile according to the procedure of Example 14 to give 10.2 g (46%) of the title product.

Anal. Calcd. for $C_{15}H_{23}Cl_4N_5.HI$: C, 33.17; H, 4.45; N, 12.90. Found: C, 33.47; H, 4.37; N, 12.45.

UTILIZATION OF THE GUANIDINES

The compounds of the present invention are useful as biocides. They are generally active as microbicides, fungicides and industrial preservatives. Certain of the compounds are of particular interest as paint film fungistats.

The compounds of the invention can be applied to the aerial portions of many growing plants to control leaf-attacking fungal organisms or dispersed in soil or applied to plant seeds to control the root and seed attacking organisms of mold and damping off. In still other operations they can be applied to orchard floor surfaces to control over-wintering spores of fungal organisms. In still further operations, the compounds of the invention or compositions containing them as toxic constituents can be included in and on plaster, ink, wallboard, textiles, paper, adhesives, soaps, synthetic detergents, cutting oils, polymeric materials, embalming fluids, oil paints and latex paints to prevent the attack of various fungal pests and the subsequent economic loss due to the degradation of such products by microorganisms. Also, the compounds can be distributed in textiles, cellulosic materials or in grain or can be employed in the impregnation of wood and lumber to preserve and protect such products from the attack of the organisms of rot, mold and decay.

The exact concentration of the toxicant to be employed in the treating compositions is not critical and may vary considerably provided the required dosage of the effective agent is supplied in the ink, adhesive, soap, cutting oil, polymeric material, paint, textile, paper, wood or growth medium or upon plant foliage. The concentration of toxicant in liquid compositions generally is from about 0.5 parts per million to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicants can be present in a concentration of from 5 to 98 percent by weight. For use as a foliar spray or in seed treatment, it is often convenient to apply the compounds as wettable powders.

The compounds may be used with a wide variety of oils, resin, solvents, pigments and coating additives in formulating organic film-forming compositions having mildew resistance. The more common types of exterior coatings for which these compounds are useful as fungicides include the drying oils, alkyds and latex-type paints. Solvents and co-solvents are used conventionally in both organic-thinned or water-thinned coating compositions, for instance, mineral spirits, polyols, benzoids, etc. Numerous additives can be incorporated in the antifungal paints for suppressing foam, for plasticizing the dried films, for emulsifying latexes, or for accelerating the film cure.

Mildew growth on exterior organic coatings is attributed to several fungi. The relative importance of different species of fungi is climatically dependent; but, Pullularia species usually account for the major number of fungus colonies on painted surfaces in the United States. In warm, moist climates such as the Gulf areas around the 30th parallel, Pullularia species account for about 75% to over 90% of mildew growth. North of the 40th parallel this species amounts to more than half the growth. In the warmer moist areas, Alternaria species, Cladosporium species, and Penicillium species are secondary causes of discoloration. In the northern climates Aspergillus species also is a secondary mildew fungus.

A number of other microorganisms, such as Rhodotorula (yeast), Monilia, Mucor and Botrytis, are minor causes of mildew. An organic surface that is a nutrient for some fungi may not be a nutrient for others. Generally, a nutrient for other fungi will also support Pullularia growth. Alternaria occurrence is higher in latex paints, whereas Cladosporium does not thrive on a typical latex film. Rhodotorula is associated mostly with drying oil paint vehicles and areas protected from weathering.

The preferred concentrations of the compounds of the invention in the dry coating film is from the minimum inhibitary concentration up to about 2 percent by weight. Higher concentrations may be employed but generally are of no greater benefit.

Utility Examples

EXAMPLE 20 - In Vitro Fungicide/microbicide Tests

In a representative operation, each of the compounds listed in Table I was tested by incorporating it as the sole toxicant in each of from fourteen to eighteen nutrient agars, each innoculated with a different one of the organisms listed in the table. After suitable incubation times, each agar is compared to a control agar to which no toxicant has been added. If growth of an organism has been retarded by at least 50%, the toxicant is rated as inhibitory to that organism. In those cases where inhibition is observed at the initial test concentration of the toxicant (500 parts per million), the test is repeated for that toxicant at successively lower concentrations to determine the minimum concentration at which inhibition results.

Table I summarizes the results of this test procedure on compounds I through VII, the title compounds of preparatory Examples 13 through 19. It will be seen that each of compounds II–IV inhibited Pullularia pullulans at a concentration of 0.5 parts per million, and compounds II, III and V inhibited Salmonella typhosa at that same level.

TABLE I
MICROBIOLOGICAL TEST DATA
Min. Concn. for Inhibition[1]

| | Bacteria | | | | | | | | Yeast | | | | Fungi | | | |
|---|---|---|---|---|---|---|---|---|---|---|---|---|---|---|---|---|
| Compound | Staphylococcus Aureus | Salmonella Typhosa | Aerobacter Aerogenes | Pseudomonas Aeruginosa | Pseudomonas Sp. Strain 10 | Bacillus Subtilis | Klep Pheumoniae M-1 MID HOSP | Serratia Mercesens NIH | E. Coli ATCC 11229 | Candida Albicans NIH | Candida Albicans | Candida Pelliculosa | Torulopsis Sp. Med Col VI | Pollularia Pullulans | Ceratucystis IPS | Penicili Chrysogesum | Trichoderm Sp. Madison P-42 | Aspergillus Fumig Med Col VI | Aspergillis Niger | Trichophton Mentagrophytes |
| I | 50 | 500 | — | — | — | 50 | — | — | 500 | — | — | — | — | 10 | 50 | — | 500 | — | — | 500 |
| II | 50 | 5 | 500 | 500 | 500 | 50 | — | 500 | 500 | 500 | 500 | 500 | 500 | 0.50 | 500 | 10 | 100 | 500 | 500 | 50 |
| III | 10 | 0.5 | 500 | — | — | 50 | 500 | 500 | 500 | 50 | 50 | 500 | 500 | 0.50 | 50 | 50 | 50 | 10 | 500 | 100 |
| IV | 10 | 0.5 | — | — | — | 50 | — | — | 500 | 100 | 100 | 500 | 100 | 0.50 | 100 | 500 | 50 | — | — | 100 |
| V | 10 | 0.5 | — | — | — | 10 | — | — | — | 50 | 50 | 100 | 50 | 5 | 50 | 50 | 50 | — | — | 50 |
| VI | 50 | 5 | — | 500 | 500 | 5 | 500 | 500 | 500 | 50 | 50 | 500 | 500 | 100 | 50 | 50 | 10 | 500 | 50 | 100 |
| VII | 5 | 5 | 500 | 500 | 500 | 5 | 500 | 500 | 500 | 5 | 5 | 500 | 500 | 50 | 50 | 100 | 50 | 500 | 50 | 50 |

NOTE:
[1] Parts per million

EXAMPLE 21 - Plant Fungicide Tests

In additional representative operations, solutions or dispersions of tests of certain compounds identified in Table I in 80/20 H₂O/isopropanol were applied to host plants in a manner appropriate to the fungus involved. The plants were innoculated with, or planted in soil innoculated with, the pathogen and stored under conditions of humidity and temperature suitable for infection and disease development. Untreated check plants were rated as showing 0% control and absence of disease — after 10 days — was rated as showing 100% control. The degree of control at various concentration levels of the toxicants on each fungus was observed as follows: Compound II gave 95% control of Apple Scabs (foliage sprayed with toxicant, then innoculated with fungus) when contacted with the test compared at a rate of 400 rpm. In a similar manner, Compounds III and VI gave 90 and 99% control, respectively, of Downey Mildew, at a rate of 400 ppm. Compound III and VIII were each found to give 100% control of Vert Wilt Valbo at 100 ppm and Compound VIII 100% control of Tobacco Black Shank at 25 ppm (the toxicant being drenched on infested soil in which the host was planted). Compound V was found to give 75% control of Apple Powdery Mildew and 90% control of Wheat Leaf Rust at a rate of 400 ppm (the toxicant being sprayed on foliage and soaked into root zone, the plant then being innoculated with fungus).

The examples in the preceding specification are for purposes of illustration and are not to be construed as limiting the invention to an extent inconsistent with the following claims.

I claim:

1. A (pyridinylamino)alkylguanidine of the formula

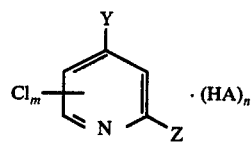

wherein:
one of Y and Z is —H, —Cl, —CCl₃ or —CN and the other is —NH—R¹—N=C(NHR²)₂,
m is 1, 2 or 3,
n is 1 or 2,
R¹ is an alkylene group of 3 to 8 carbons,
R² is —CH₃ or —C₂H₅, independently in each occurrence, and
HA is a pharmaceutically acceptable acid.

2. A compound as in claim 1 in which R¹ is a hexamethylene group.

3. A compound as in claim 1 in which the —NH—R¹—N=C(NHR²)₂ group is alpha to the ring nitrogen.

4. A compound as in claim 1 in which one of Y and Z is —NH—R¹—N=C(NHR²)₂ and the other is —CN or —CCl₃.

5. A compound as in claim 3 in which R¹ is a hexamethylene group.

6. A compound as in claim 4 in which R¹ is a hexamethylene group.

7. A compound of claim 1 in which HA is HCl, HBr, HI, H₂SO₄ or H₃PO₄.

8. A compound of claim 5 which is a salt of N,N'-dimethyl-N"-(6-((3,5,6-trichloro-2-pyridyl)amino)-hexyl)-guanidine with a pharmaceutically acceptable acid.

9. A compound of claim 2 which is a salt of N,N'-dimethyl-N"-(6-((3,5,6-trichloro-4-pyridyl)amino)-hexyl)-guanidine with a pharmaceutically acceptable acid.

10. A compound of claim 2 which is a salt of N,N'-dimethyl-N"-(6-((2,3,5-trichloro-6-cyano-4-pyridyl)-amino)hexyl)-guanidine with a pharmaceutically acceptable acid.

11. A compound of claim 2 which is a salt of N"-(6-((-6-chloro-4-trichloromethyl-2-pyridyl)amino)hexyl-N,N'-dimethyl-guanidine with a pharmaceutically acceptable acid.

* * * * *

UNITED STATES PATENT AND TRADEMARK OFFICE
CERTIFICATE OF CORRECTION

PATENT NO. : 4,108,859
DATED : August 22, 1978
INVENTOR(S) : Yulan C. Tong

It is certified that error appears in the above-identified patent and that said Letters Patent are hereby corrected as shown below:

Column 11, Table I, Compound II, the last number in the column should be -- 500 --, rather than "50".

Column 11, Table I, Compound III, the last number in the column should be -- 50 --, rather than "100".

Signed and Sealed this

Tenth Day of April 1979

[SEAL]

Attest:

RUTH C. MASON
Attesting Officer

DONALD W. BANNER
Commissioner of Patents and Trademarks